United States Patent [19]

Moreno

[11] Patent Number: 4,820,276
[45] Date of Patent: Apr. 11, 1989

[54] FILTER ASSEMBLY FOR USE WITH A HYPODERMIC SYRINGE

[76] Inventor: Enrique Moreno, Post Office Box 1750, Mayaguez, P.R. 00709

[21] Appl. No.: 153,093

[22] Filed: Feb. 8, 1988

[51] Int. Cl.⁴ ............................................. A61M 5/00
[52] U.S. Cl. ..................................... 604/190; 222/386
[58] Field of Search ............... 604/190, 187, 246, 247, 604/248, 249, 236; 222/386, 387

[56] References Cited

U.S. PATENT DOCUMENTS

| | | | |
|---|---|---|---|
| 3,747,812 | 7/1973 | Karman et al. | 222/387 |
| 4,008,718 | 2/1977 | Pitesky | 604/190 |
| 4,137,917 | 2/1979 | Cohen | 604/190 |
| 4,609,371 | 9/1986 | Pizzino | 604/191 |

Primary Examiner—John D. Yasko
Attorney, Agent, or Firm—Scrivener and Clarke

[57] ABSTRACT

A filter assembly for a hypodermic syringe consists of a compartmented filter unit whose compartments contain filter material. Ports open through a lower wall of the respective compartment, and rotatably fixed to the filter unit is a disc-like fluid passage member having a first fluid passage therein one end of which is selectively movable into alignment with the respective ports and the other end of which is in communication with a second fluid passage through a needle-receiving hub fixed to the lower face of the fluid passage member. By indexing the fluid passage member, fluid pumped into and out of the syringe barrel may be subjected to filtration through fresh filter areas in successive compartments.

7 Claims, 1 Drawing Sheet

FILTER ASSEMBLY FOR USE WITH A HYPODERMIC SYRINGE

FIELD OF THE INVENTION

This invention relates to hypodermic syringes and more particularly to a filter assembly for use with or as part of a hypodermic syringe.

BACKGROUND OF THE INVENTION

It is desirable that when liquid is drawn into a hypodermic syringe barrel for subsequent injection into a patient the liquid be filtered to remove stray solids, e.g. rubber from a cap through which a needle is inserted for the removal of liquid from a container, and it is also desirable that the liquid, before it is expelled from the syringe barrel, be filtered again. Obviously different filter areas should be used for the entry and exit of liquid into and out of the syringe.

The recognition of the desirability of presenting fresh filter areas to fluid as it passes into and out of a syringe barrel is embraced in the patent to Cohen U.S. Pat. No. 4,137,917. In that patent a continuous sheet of filter material is attached to an apertured slider having a pusher handle extending outwardly of a housing having an apertured socket on one side to receive the usual needle hub of the syringe and an apertured nipple on the other side which is a duplicate of the usual needle hub on the syringe. As the slider is slid into the housing, successive apertures in the slider, aligned with separate filter areas of the sheet of filter material, are brought into alignment with the openings through the hubs on the syringe and housing and thus the fluid is caused to pass through fresh filter areas as fluid is pumped into and out of the syringe barrel.

There are a number of problems with such an arrangement. For example, a continuous layer of filter material is used and it is clear that liquid passing through one area of the filter material will naturally flow by capillary action laterally through all of the filter material. Thus the entire layer of filter material can be contaminated by infectious organisms. Further, the handle which must be slid from outside the housing into the housing can be a source of infection, and, finally, the housing itself constitutes an awkward visual and physical obstruction.

BRIEF DESCRIPTION OF THE INVENTION

The object of the present invention is to provide a filter assembly for use with a hypodermic syringe, either as a separate entity, or as part of the syringe itself, which has none of the foregoing problems.

Broadly, the invention consists of a filter assembly which may be a separate assembly adapted to be attached to a syringe, or may be an integral part of the syringe. The assembly comprises a filter unit and a fluid passage member. The filter unit is preferably circular and of substantially the same diameter as the syringe barrel and includes a bottom wall carrying on one face vertical walls to define a plurality of open-top compartments, some or all of which contain filter material, the filter material in any one compartment being separated by the vertical and bottom walls from the material in any of the other compartments. The bottom wall has ports therethrough leading, respectively, into the separate compartments, the centers of all of the ports being on a common radius about a center, which, when the assembly is in its position of use is coaxial with the barrel. The fluid passage member is of disc-like configuration and is rotatably fixed to the filter unit. The member includes a fluid passage, preferably sloping, having one end alignable with any one of a selected port through the bottom wall of the and its other end at all times in communication with a fluid passage through a needle hub carried on the lower face of the fluid passage member.

BRIEF DESCRIPTION OF THE DRAWINGS

The invention will be better understood when its detailed description is read in conjunction with the accompanying drawings, wherein.

Figure 1:
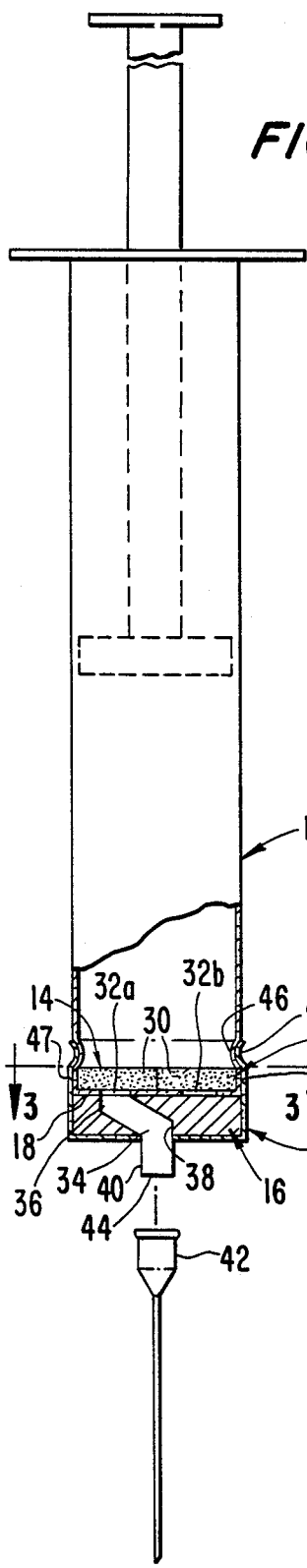
FIG. 1 is an elevational view of a hypodermic syringe, partly broken away to show the present invention in vertical cross-section.

Referring now to the drawings the numeral 10 refers to a hypodermic syringe, which carries, either separately or integrally at its lower end, a filter assembly constructed in accordance with the invention and designated broadly by the numeral 12. The assembly comprises a filter unit 14 and a relatively rotatable fluid passage member 16.

The filter unit is comprised of a bottom wall 18 having inner and outer faces. Side walls, such as circular wall 20 and radial walls 22, are fixed to the inner face of bottom wall 18 to define a plurality of open-top compartments 24, 26, 28 which are laterally fluidly separated from each other by the side and bottom walls. Any number of compartments can be provided three being shown. One or all of the compartments is or are provided with filter material 30 depending on the number of times fluid to be filtered flows into and out of the syringe barrel. Where a syringe may be used either to inject medicine or to draw blood, one compartment, such as 24, is provided with no filter. The bottom wall 18 has ports 32, 32a and 32b therethrough, one leading into each of the respective compartments, the centers of the ports being on a common radius whose center, when the filter unit is in its position of use, is coaxial with the syringe barrel 10.

Figure 2:
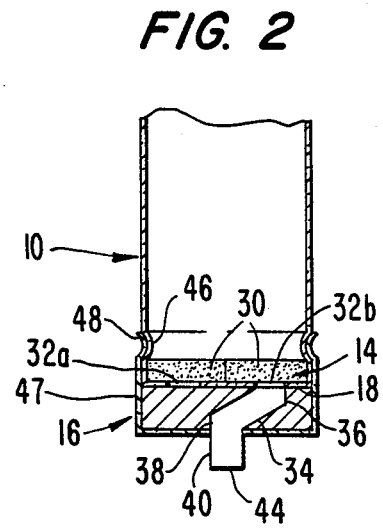
FIG. 2 is a broken view similar to FIG. 1 showing the rotatable member in changed position.

The fluid passage member 16 is of disc-like configuration and rotatably carried by the filter unit 14. The member 16 has a first fluid passage 34 therein, preferably sloping as shown, having a first end 36 which is selectively movably by relative rotation between the member 16 and filter unit 14 into fluid connection with any selected one of the ports 32, 32a, 32b. In FIG. 1, the end 36 is seen in communication with port 32a; in FIG. 2 it is communicating with port 32b. The first fluid passage 33 has a second end 38 and the member 16 includes a hub 40 for receiving a needle 42 and has a second fluid passage 44 therethrough, the second end 38 of the first fluid passage 34 in the member 16 communicating with the second fluid passage 44 through the hub. Means are provided for mounting the filter assembly onto the end of a syringe barrel with the open tops of the compartments 24, 26, 28 in communication with the interior of the barrel.

One means for mounting the assembly onto the barrel could be by encapsulating the assembly and providing a socket on its upper side and a needle-receiving hub or nipple on its lower side. The socket would engage the regular needle hub carried by the syringe. Another mounting means would be as shown where the circular side wall 20 of the filter unit is extended in an axial direction above the radial walls 22 and the extended part is provided with a first annular discontinuity such as the annular groove 46 shown. The fluid passage member is also provided with an upstanding annular side wall 47 having a second annular discontinuity, such as the annular ridge 48 shown, which is complementary to the first discontinuity 46, the discontinuities 46, 48 being slidably engaged so as to permit the fluid passage member to be rotated relative to the filter unit.

It is within the purview of the invention for the filter assembly to be formed as part of the hypodermic syringe. As shown, the circular side wall 20 of the filter unit may be an integral part of the barrel with the discontinuity 46 being molded into the barrel. The bottom wall 18 of the filter unit would then be integral with the barrel and defines the lower end thereof.

Figure 3:
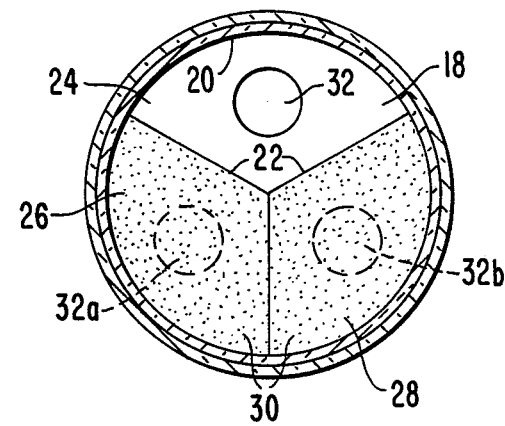
FIG. 3 is an enlarged horizontal cross-sectional view taken substantially on the line 3—3 of FIG. 1.

The manner of use of the invention should be clear. With reference to FIG. 3, if liquid from some source is to be drawn into the barrel the fluid passage member 16 would be positioned so that the end 36 of the passage connects with one compartment, say 26, through its port 32a. The liquid would then be drawn into the barrel and as it is done so it is filtered by the filter material in compartment 26. The operator then indexes the member 20 until the passage end 36 connects with port 32b whereupon fluid in the barrel may be ejected through the filter material in compartment 28. It does not matter that the lower side of the filter material in compartment 26 contains filtrate, because this cannot be freed to flow upwardly through the filter material in compartment 26 by the fluid being forced to flow in the opposite direction through the filter material in compartment 28. Because the filter material in adjacent compartments are isolated by the compartment walls it is impossible for contaminants filtered out in one compartment to flow laterally by wicking action into the filter material of the adjacent compartment.

The compartment 18 is shown without filter material in the event that the syringe should be used for drawing blood, under which circumstances filtration is decidedly undesirable.

It will be apparent that if it should be desirable to filter ambient air drawn into the barrel, the compartment 18 would be supplied with filter material. After the indrawn air has been filtered it would be expelled into the liquid container through one of the other filter elements after the fluid passage member had been suitably indexed. The liquid would then be drawn into the barrel through that same filter material but before being injected into the patient the member 16 would be indexed again to connect compartment 28 with the needle through the passage 34 in the fluid passage member 16.

An advantage of the arrangement of the invention is that the entire assembly can be of the same diameter as the barrel and thus cannot constitute a visual or physical obstruction. Further, because the fluid passage member is rotatable by finger pressure exclusively on its exterior surface, there is nothing to push into the assembly which might carry into it infectious organisms. Further, the assembly is versatile since it permits either the filtration of an injectable fluid, both as it is drawn into the barrel or expelled, or the use of the syringe to draw blood without filtration, and without the necessity of removing the assembly, which makes it particularly attractive where the assembly is an integral part of the syringe.

It will be appreciated that the invention is susceptible of a variety of changes and modifications without, however, departing from the scope and spirit of the appended claims.

I claim:

1. A filter assembly for use with a hypodermic syringe comprising a filter unit which includes a bottom wall having inner and outer faces, side walls fixed to one of said faces to define a plurality of open top compartments which are fluidly separated from each other by said side and bottom walls, filter material in at least one of said compartments, said bottom wall having ports therethrough leading into each of the respective compartments, the centers of said ports being on a common radius whose center, when said unit is in its position of use, is coaxial with a syringe barrel, a fluid passage member rotatably carried by said filter unit and having a first fluid passage therein having a first end which is selectively movable by relative rotation between said member and unit into fluid connection with any one of the ports through the bottom wall of said filter unit, said first fluid passage having a second end, said member including a needle-receiving hub having a second fluid passage therethrough the second end of said first fluid passage at all times communicating with said second fluid passage through said hub, and means for mounting said assembly onto the end of a syringe barrel with the open tops of said compartments in communication with the interior of said barrel.

2. The filter assembly of claim 1, wherein at least two of the compartments contain filter material.

3. The filter assembly of claim 1, wherein there are three compartments, two of which contain filter material and the third of which contains no filter material.

4. The filter assembly of claim 1, wherein said side walls comprise a first circular upstanding wall coaxial with the center of said common radius and a plurality of second radially extending walls having outer ends integrally joined to said circular wall and inner ends integrally joined to each other at the center of said common radius, the lower edges of said second walls being integrally joined to said one of the faces of said bottom wall.

5. The filter assembly of claim 4, wherein said circular wall extends in an axial direction above said radial walls and filter material, the axially extending part being provided with a first annular discontinuity and said member has an upstanding annular wall with a second annular discontinuity complementary to said first discontinuity, said discontinuities being slidably engaged so as to permit said member to be rotated relative to said unit.

6. The combination of the assembly of claim 1 and a hypodermic syringe.

7. The filter assembly of claim 5, wherein said circular side wall is a continuation of the barrel wall of a syringe and said bottom wall is defined by an integral bottom wall of said syringe.

* * * * *